United States Patent [19]

Sun

[11] Patent Number: 4,666,925
[45] Date of Patent: May 19, 1987

[54] 1-ISOPROPYL-2-INDANOL AND -INDANTHIOL ETHER INSECTICIDES

[75] Inventor: King M. Sun, Modesto, Calif.

[73] Assignee: E. I. Du Pont de Nemours and Company, Wilmington, Del.

[21] Appl. No.: 778,993

[22] Filed: Sep. 23, 1985

Related U.S. Application Data

[63] Continuation-in-part of Ser. No. 643,923, Aug. 24, 1984, abandoned.

[51] Int. Cl.⁴ .................. C07D 213/64; A01N 43/40; A01N 31/14; C07C 43/263
[52] U.S. Cl. ..................................... 514/345; 514/351; 514/357; 514/712; 514/716; 514/717; 514/718; 514/721; 546/300; 546/301; 546/302; 558/428; 568/44; 568/49; 568/586; 568/587; 568/592; 568/633; 568/634
[58] Field of Search ............... 568/586, 587, 592, 633, 568/634, 44, 49; 558/428; 546/300, 301, 302; 514/345, 351, 357, 712, 716, 717, 718, 721

[56] References Cited

U.S. PATENT DOCUMENTS 3,636,002  1/1972  Godefroi .............................. 548/341

*Primary Examiner*—Alan L. Rotman

[57] ABSTRACT

Compounds of the formula

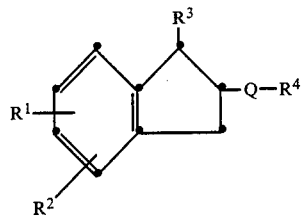

wherein Q is O or S, $R^1$ and $R^2$ are H, halogen, (halo)alkyl or (halo)alkoxy or together are methylenedioxy, $R^3$ is isopropyl optionally fluoro-substituted and $R^4$ are the residues of certain alcohols of the pyrethroid type, are useful as insecticides.

10 Claims, No Drawings

1-ISOPROPYL-2-INDANOL AND -INDANTHIOL ETHER INSECTICIDES

CROSS-REFERENCE TO RELATED APPLICATION

This application is a continuation-in-part of U.S. Ser. No. 643,923, filed Aug. 24, 1984 now abandoned.

BACKGROUND OF THE INVENTION

Field of the Invention

The present invention relates to novel 1-isopropyl-2-indanol and -indanthiol derived ethers, their use as pesticides and to pesticidal compositions containing these new ethers.

SUMMARY OF THE INVENTION

The present invention is directed to a compound of the formula I

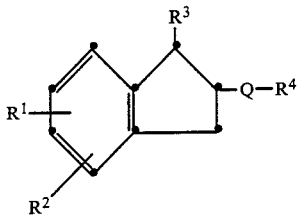

wherein Q is O or S, $R^1$ and $R^2$ each independently is a hydrogen atom, a halogen atom selected from chlorine, bromine and fluorine, a nitro group, a cyano group, an alkyl or an alkoxy group in which the alkyl portion contains 1 to 6 carbon atoms, each optionally substituted by one or more halogen atoms, or $R^1$ and $R^2$ when taken together form a methylenedioxy group; $R^3$ is isopropyl optionally substituted by one or more fluorine atoms; and $R^4$ is a hydrogen atom, or an alkyl, aryl or aralkyl sulfonyl group containing up to 14 carbon atoms in which any aryl is a single or fused aromatic carbocyclic ring or a group of the formula II

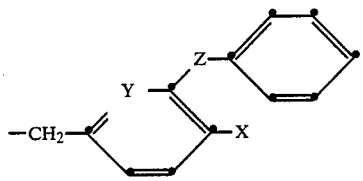

in which X is a hydrogen atom or a fluorine atom, Y is —CH—, —C(CH$_3$)—, or —N—, and Z is a bond, an oxygen or sulfur atom, —NH—, or the carbonyl group. The compounds are useful as insecticides or miticides (in the trans or cis-trans form) or are intermediates therefor.

Non-limiting examples of compounds of formula I include:
  6-chloro-1-isopropyl-2-((6-phenoxypyridin-2-ylmethoxy)indane
  5-methyl-1-isopropyl-2-(((4-fluoro-3-phenyl)benzyl)oxy)indane,
  5,6-dichloro-1-isopropyl-2-((3-phenoxybenzyl)oxy)indane,
  5-fluoro-1-isopropyl-2-(((4-fluoro-3-phenoxy)benzyl)oxy)indane,
  5-methoxy-1-isopropyl-2-((((4-fluoro-3-phenoxy)benzyl)oxy)indane,
  5-methoxy-1-isopropyl-2-((6-phenoxypyridin-2-yl)methoxy)indane,
  6-ethoxy-1-isopropyl-2-((((4-fluoro-3-phenoxy)-benzyl)oxy)indane,
  5-ethoxy-1-isopropyl-2-((3-phenylbenzyl)oxy)indane,
  5-chloro-1-isopropyl-2-((6-phenoxypyridine-2-yl)methylthio)indane
  5-methyl-1-isopropyl-2-(((4-fluoro-3-phenyl)benzyl)oxy)indane,
  5,6-dichloro-1-isopropyl-2-((3-phenoxybenzyl)thio)indane,
  6-fluoro-1-isopropyl-2-(((4-fluoro-3-phenoxy)benzyl)thio)indane,
  5-methoxy-1-isopropyl-2-((((4-fluoro-3-phenoxy)-benzyl)thio)indane,
  5-methoxy-1-isopropyl-2-((6-phenoxypyridin-2-yl)methylthio)indane,
  5-ethoxy-1-isopropyl-2-((((4-fluoro-3-phenoxy)-benzyl)thio)indane,
  6-ethoxy-1-isopropyl-2-((3-phenylbenzyl)thio)indane, and the corresponding indanols, indanthiols, and sulfonates and thiosulfonates derived from such indanols.

In one embodiment of the present invention of the compounds of formula I, $R^1$ is a chlorine, bromine or fluorine atom or an alkyl or alkoxy group containing from 1 to 4 carbon atoms optionally substituted by from 1 to 3 chlorine or fluorine atoms; and $R^2$ is a hydrogen atom or a chlorine, bromine or fluorine atom. Preferably, $R^1$ is a bromine or fluorine atom or, especially, a chlorine atom. Preferably, $R^2$ is a hydrogen atom or a chlorine atom.

The compounds of formula I include the novel 1-isopropyl-2-indanols and indanthiols, per se, in which $R^4$ is a hydrogen atom, or to the conventional reactive derivatives thereof in which $R^4$ is an alkyl, aryl or aralkyl sulfonyl group containing up to 14 carbon atoms, in which any aryl is a single or fused aromatic carbocyclic ring such as mesyloxy, tosyloxy and the like, which are useful intermediates to the insecticidal or miticidal ethers of formula I in which $R^4$ is a group of formula II. The preferred intermediates are the 1-isopropyl-2-indanols, per se, in which $R^4$ is a hydrogen atom.

The compounds of formula I in which $R^4$ is a group of formula II are insecticidally or miticidally active ethers. In one embodiment of these ethers, Q is O and Z is preferably an oxygen atom or a bond. For example, $R^4$ is a 3-phenoxybenzyl group, including the 4-fluoro-3-phenoxybenzyl group, or a 6-phenoxypyridin-2-ylmethyl group.

The ethers of formula I in which $R^4$ is a group of formula II are prepared by conventional procedures in which a compound of formula III

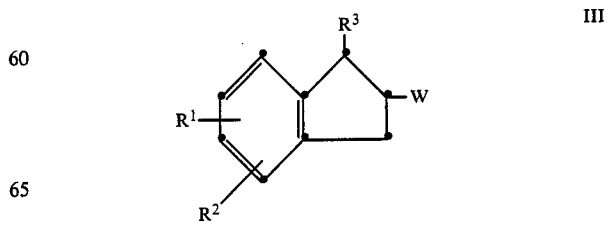

is reacted with a compound of formula IV

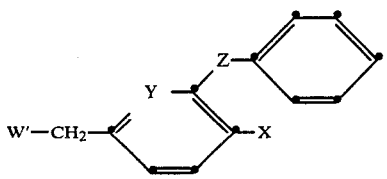

in which W is —OH or —SH and W' is a halogen or $R^5$-sulfonyloxy group where $R^5$ is alkyl, aryl or aralkyl of up to 14 carbon atoms in which any aryl is a single or fused aromatic carbocyclic ring, preferably methyl or para-methylphenyl, 1-naphthyl, and the like, and $R^1$, $R^2$, $R^3$, X, Y and Z have the above meanings.

The ether formation is preferably carried out in the presence of a strong base, for example, an alkali metal hydride, hydroxide or carbonate, such as sodium hydride, sodium hydroxide or sodium carbonate. Preferably, an inert solvent is present. Typical inert solvents include ethers, sulfoxides, aromatic hydrocarbons, chlorinated hydrocarbons and the like, such as diethyl ether, tetrahydrofuran, dimethyl sulfoxide, toluene, methylene chloride and the like. It may be desirable to include a catalyst, such as quaternary ammonium compounds, for example, tetra-n-butylammonium iodide and the like. Suitable temperatures for the reaction are, for example, from about 0° C. to about 120° C. The products are recovered by conventional techniques, such as extraction, chromatographic separation and the like.

The compounds of formula I wherein $R^4$ is a hydrogen atom are prepared by first treating an optionally aromatic ring substituted indene or 1-indanone with an appropriate isopropylating agent under conventional alkylating conditions to introduce the group $R^3$. For example, when starting from an indene, the alkylating agent is $R^3$Hal in which $R^3$ is, e.g. an isopropyl group, and Hal is preferably hlorine, bromine or iodine, preferably in the presence of an inert solvent, such as diethyl ether or tetrahydrofuran. The resulting 1-isopropylated-1H-indene is treated first with borane in the presence of an inert solvent, such as tetrahydrofuran, and then with sodium hydroxide and hydrogen peroxide. When starting from an indanone, (1) a 1-indanone is treated with an alkylating agent $R^3$MgHal in which $R^3$ is, e.g., an isopropyl group, and Hal is preferably chlorine or bromine, preferably in an inert solvent, such as diethyl ether or tetrahydrofuran, followed by refluxing with an acid, such as p-toluenesulfonic acid, in an aromatic solvent, such as benzene, or (2) a 2-indanone is reacted with $R^3$Hal as defined above, followed first by treatment with sodium borohydride in ethanol and, then, if the trans is desired, refluxing with methylenesulfonyl chloride in pyridine to give the intermediate indene. The resulting 1-isopropylated-1H-indene from (1) or (2) is treated with borane in the presence of an inert solvent, followed by sodium hydroxide and hydrogen peroxide.

The above 1-alkyl-2-indanols are used directly for synthesis of the ethers of formula I in which $R^4$ is a group of formula II or are first converted by conventional procedures into its reactive derivatives in which $R^4$ is a sulfonyl group, which reactive derivatives are also useful for preparing the ethers of formula I by conventional procedures known in the art.

The compounds of formula I in which Q is S are prepared by first forming 1-alkyl-2-indanol sulfonates as described above. The sulfonates are then converted to the 1-alkyl-2-indanthiols by (a) treatment with NaSH of (b) treatment with $C_6H_5CH_2SNa$ followed by hydrogenation. The various other derivatives are made from these 1-alkyl-2-indanthiols by conventional procedures known in the art.

The compounds of formula I can exist as optical isomers thereof due to the presence of two asymmetric carbons in the structure of the 1-alkyl-2-indanol moiety. The present invention includes all the insecticidally active ethers of formula I and the intermediates thereto and, thus, includes the cis-trans and trans optical isomers of the compounds of formula I. It appears that the trans isomers are usually more insecticidally effective than the corresponding cis-trans isomer mixture.

The starting materials of formula IV are conventional alcohols of the pyrethroid type and their reactive derivatives whose preparation is well known in the art, for example, in U.S. Pat. Nos. 3,666,789, 4,218,469, 4,130,657, 4,214,004, 3,163,787 and Japanese patent 58/35,175, and the like.

The starting indenes and indanones are known in the art or can be prepared by introducing the desired ring substituents, $R^1$ and $R^2$, onto the indene or indanone by conventional procedures or by cyclizing the appropriately substituted 3-phenylpropionic acid derivatives followed by alkylation as described above to form the intermediate optionally aromatic ring-substituted alkylindene.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analysis as necessary.

EMBODIMENT 1

6-Chloro-3-isopropyl-1H-indene

A solution of 5-chloro-1-indanone (3.59 g) in anhydrous tetrahydrofuran (40 ml) was added to a solution of isopropyl magnesium chloride (103 ml, 2M ethereal solution) under nitrogen at a rate to produce gentle refluxing. After the addition, the reaction solution was further stirred at room temperature for 1¼ hr, then poured into water (200 ml) and extracted with diethyl ether (3×150 ml). The combined ether solutions was washed with water, and condensed to an oil. This oil dissolved in benzene (250 ml) with a catalytic amount of p-toluenesulfonic acid was refluxed for 1.5 hr and then poured into water (200 ml). A few drops of diethylamine were added. The aqueous solution was separated and extracted with diethyl ether (3×100 ml). The combined organic phases were washed sequentially with dilute hydrochloric acid, saturated sodium bicarbonate solution and water, then dried (MgSO₄) and condensed under reduced pressure. The residue was purified on a flash column (eluted with 5% ether in hexane) to give 6-chloro-3-isopropyl-1H-indene (2.94 g).

EMBODIMENT 2 trans-5-Chloro-1-isopropyl-2-indanol

A solution of 6-chloro-3-isopropyl-1H-indene (6.45 g) in anhydrous tetrahydrofuran (15 ml) was added to a solution of borane:tetrahydrofuran complex (84.3 ml of 1.0M solution) at 0° C. under nitrogen atmosphere. The temperature of the reaction solution was kept below 5° C. during the addition. After the addition, the solution was further stirred at 0° C. for 0.5 hr and at room temperature for 2 hr. The solution was cooled to 0° C. and water (100 ml) was added, followed by 6N NaOH solution (100 ml) and hydrogen peroxide (100 ml, 30% aqueous solution). The mixture was stirred for one hour, then potassium carbonate (100 g) was added, ad the whole mixture was extracted with diethyl ether (3×150 ml). The combined ether extracts was washed with water, dried (MgSO$_4$) and condensed to give an oil. This oil was purified by flash chromatography to give trans-5-chloro-1-isopropyl-2-indanol (6.67 g).

EMBODIMENT 3 trans-5-Chloro-1-isopropyl-2-((6-phenoxypyridin-2-yl)-methoxy)indane

A solution of trans-5-chloro-1-isopropyl-2-indanol (0.75 g) in anhydrous tetrahydrofuran (5 ml) was added to a suspension of sodium hydride (0.28 g, oil free) in anhydrous tetrahydrofuran (5 ml). The mixture was stirred for 0.5 hr and 2-(bromomethyl)-6-phenoxypyridine (1 g) in anhydrous tetrahydrofuran (5 ml) was added, followed by a catalytic amount of tetra-n-butylammonium iodide. The mixture was stirred at room temperature for 18 hours, mixed with water (100 ml) and extracted with diethyl ether (3×50 ml). The ether extract was dried (MgSO$_4$) and condensed under reduced pressure to give an oil that was purified by flash chromatography to give trans-5-chloro-1-isopropyl-2-((6-phenoxypyridin-2-yl)-methoxy)indane (0.94 g).

EMBODIMENT 4 trans-5-Chloro-1-isopropyl-2-((3-phenoxyphenyl)methoxy)indane

Following procedures similar to those described in Embodiment 3 above, the desired product was prepared from trans-5-chloro-1-isopropyl-2-indanol and 3-phenoxybenzyl bromide.

EMBODIMENT 5 trans-5-Chloro-1-isopropyl-2-((4-fluoro-3-phenoxyphenyl)methoxy)indane

Following procedures similar to those described in Embodiment 3 above, the desired product was prepared from trans-5-chloro-1-isopropyl-2-indanol and 4-fluoro-3-phenoxybenzyl bromide.

EMBODIMENT 6

1-Isopropyl-1H-indene n-Butyl lithium (37 ml in hexane) was added to a solution of 1H-indene (6.30 ml) in anhydrous diethyl ether (40 ml) under nitrogen atmosphere at 15° C. The solution was stirred at room temperature for 10 min, 2-bromopropane (18.8 g) in anhydrous ether (100 ml) was added, and stirring was continued for 72 hours. Water (30 ml) was added, the phases were separated, and the aqueous phase was extracted with ether. The combined ether solutions was washed with water, dried (MgSO$_4$) and condensed. The residue was distilled (50°-55° C., 0.03 mmHg) to give 1-isopropyl-1H-indene (5.95 g).

EMBODIMENT 7 trans-1-Isopropyl-2-((3-phenoxy)phenyl)methoxy)indane

Following procedures similar to those described in Embodiments 2 and 3 above, 1-isopropyl-1H-indene was converted by hydroboration to 1-isopropyl-2-indanol and the trans form recovered and reacted with 3-phenoxybenzyl bromide to give the desired product.

EMBODIMENTS 8–19

Following procedures similar to those described in Embodiments 1–7, additional compounds of the invention were prepared as set forth in Table 1 below.

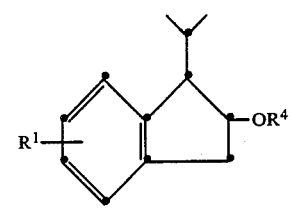

| R$^1$ | R$^4$ | Boiling Point*, °C. (760 mm Hg) |
|---|---|---|
| 5,6-Cl$_2$ | H | (white solid) |
| 5,6-Cl$_2$ | 3-phenoxybenzyl | (pale yellow oil) |
| 5,6-Cl$_2$ | 4-F—3-phenoxybenzyl | (brown oil) |
| 5-F | H | 270° |
| 5-F | 3-phenoxybenzyl | 510° C. |
| 5-F | 6-phenoxypyridin-2-ylmethyl | (yellow oil) |
| 5-OCH$_3$ | H | 320° C. |
| 5-OCH$_3$ | 3-phenoxybenzyl | 570° C. |
| 5-OC$_2$H$_5$ | H | 330° C. |
| 5-OC$_2$H$_5$ | 3-phenoxybenzyl | 580° C. |
| 5-OC$_2$H$_5$ | 4-F—3-phenoxybenzyl | 580° C. |
| 5-OC$_2$H$_5$ | 6-phenoxypyridin-2-ylmethyl | 590° C. |

*These boiling points are estimated based on their G.C.M.S. retention time.

EMBODIMENT 20 trans-5,6-Dichloro-1-isopropyl-2-((6-phenoxypyridin-2-yl)-methoxy)indane

A solution of trans-5,6-dichloro-1-isopropyl-2-indanol (0.73 g), in anhydrous tetrahydrofuran (7 ml) was added to a suspension of sodium hydride (0.24 g, oil free) in anhydrous tetrahydrofuran (10 ml). The mixture was stirred for 40 minutes and a solution of 2-(bromomethyl)-6-phenoxypyridine (0.84 g) in anhydrous tetrahydrofuran was added, followed by a catalyst amount of tetra-n-butylammonium iodide, The mixture was stirred at room temperature for 18 hours, mixed with water (100 ml) and extracted with diethyl ether (3×50 ml). The combined ether extracts were dried (MgSO$_4$) and condensed under reduced pressure to give an oil which was purified by flash chromatography to give trans-5,6-dichloro-1-isopropyl-2-((6-phenoxypyridin-2-yl)-methoxy)-indane (1.07 g).

For application, the compound of Formula I in which R$^4$ is a group of Formula II ordinarily is applied most effectively by formulating it with a suitable inert carrier or surface-active agent, or both. The invention, therefore, also includes compositions suitable for combatting insect or mite pests, such compositions comprising an inert carrier or surface-active agent, or both, and as active ingredient at least one compound of Formula I. The invention also provides a method of combatting insect or mite pests at a locus, which comprises applying to the insects or mites or to the locus a compound of Formula I in which $R^4$ is a group of Formula II or an insecticidal or miticidal composition according to the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25–75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formations contain 90% or more by weight of finely divided active material, 3–7% by weight of a blend of surfactants, which act as wetting, dispersing, suspending and binding agents, and 1–3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

The compositions of the invention may also contain other ingredients, for example, other compounds possessing pesticidal, especially insecticidal, acaricidal or fungicidal properties, as are appropriate to the intended purpose.

The method of applying a compound of this invention to control insect pests comprises applying the compound, ordinarily in a composition of one of the aforementioned types, to a locus or area to be protected from the insects or mites, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected—i.e., the dosage which the insect contracts—is of the order of 0.001 to 0.5% based on the total weight of the formulation, though under some circumstances the effective concentration will be as little as 0.0001% or as much as 2%, on the same basis.

Activity of compounds of Formula I wherein $R^4$ is a group of formula II with respect to insect and acarine (mite) pests was determined by using standardized test methods to measure the toxicity of the compounds as follows:

I. Houseflies (*Musca domestica* (Linne)) were tested by placing 50 4- to 5-day old adult houseflies into a spray cage and spraying with 0.6 ml of a solution of test compound. After spraying, knockdown effect was observed and the flies were anesthetized with $CO_2$ and transferred to a recovery cage containing a milk pad for food. The cages were held for 18–20 hours after which mortality counts were made. Both dead and moribund flies were counted. The test were conducted employing several different dosage rates for each test compound.

II. Pea aphids (*Acyrthosiphon pisum* (Harris)) were tested by placing about 100 adult aphids on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing several different dosage rates for each test compound.

III. Third instar corn earworm larvae (*Heliothis zea* (Boddie)) were tested by spraying a broad bean plant with dilutions of an acetone solution of the test compound in water containing an emulsifier. Immediately after spraying, 5 larvae were transferred to the plant and held for 44–46 hours, at which time the dead and moribund larvae were counted. The tests were conducted employing several different dosage rates for each test compound.

IV. Adult female two-spotted spider mites (*Tetranychus urticae* (Koch)) were tested by placing 50–75 mites on the bottom side of leaves of pinto bean plants. The leaves were sprayed with dilutions of an acetone solution of the test compound in water containing an emulsifier and kept under laboratory conditions for about 20 hours, at which time mortality counts were made. The tests were conducted employing several different dosage rates for each compound.

In each set of tests, identical tests were conducted using Parathion as a standard for comparison.

In each instance, the toxicity of the test compound was compared to that of a standard pesticide, parathion, the relative toxicity of the test compound then being expressed in terms of the relationship between the amount of the test compound and the amount of the standard pesticide required to produce the same percentage (50%) of mortality in the test insects. By assigning the standard pesticide an arbitrary rating of 100, the toxicity of the test compound was expressed in terms of the Toxicity Index, which compares the toxicity of the test compound of the invention with that of the standard pesticide. That is to say, a test compound having a Toxicity Index of 50 would be half as active, while one having a Toxicity Index of 200 would be twice as active, as the standard pesticide. The results are set forth in Table I.

TABLE I

| Compound Number | Toxicity Index | | | |
| --- | --- | --- | --- | --- |
| | House-fly | Pea Aphid | Corn Earworm | Two-spotted Mite |
| 4 | 2.6 (K) | 4 | 49 | 0 |
| 5 | 2.2 (K) | 22 | 24 | 0 |
| 3 | 8.1 | 6 | 95 | 0 |
| 7 | (K) | 1 | 1 | 0 |
| 9 | 4.6 | 28 | 108 | + |
| 10 | 20.0 | 130.0 | 240.0 | 30 |
| 20 | 30.0 | 40.0 | 420.0 | 0 |
| 12 | + | + | 12.0 | 0 |
| 13 | 11.0 | — | 31.0 | 0 |
| 15 | 3.0 | 1.0 | 18.0 | 0 |
| 17 | 3.0 | 10.0 | 50.0 | 0 |
| 18 | 11.0 | 70.0 | 50.0 | 0 |
| 19 | 18.0 | 50.0 | 50.0 | + |

(K) = knockdown activity.
+ = some activity
— = "no test"

What is claimed is:

1. A compound of the formula I

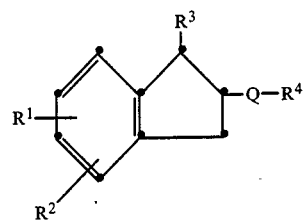

wherein Q is O or S, $R^1$ and $R^2$ each independently is a hydrogen atom, a halogen atom selected from chlorine, bromine and fluorine, a nitro group, a cyano group, an alkyl or an alkoxy group in which the alkyl portion consists of 1 to 6 carbon atoms, each optionally substituted by one or more halogen atoms, or $R^1$ and $R^2$ when taken together form a methylenedioxy group; $R^3$ is isopropyl optionally substituted by one or more fluorine atoms; and $R^4$ is a group of the formula II

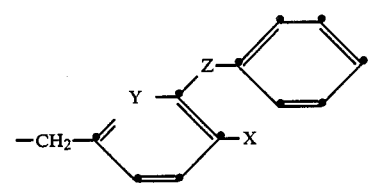

in which X is a hydrogen atom or a fluorine atom, Y is —CH—, —C(CH$_3$)—, or —N—, and Z is a bond, an oxygen or sulfur atom, said compound in the trans or cis-trans form.

2. A compound according to claim 1 wherein $R^1$ is a chlorine, bromine or fluorine atom or an alkyl or alkoxy group consisting of 1 to 4 carbon atoms optionally substituted by from 1 to 3 chlorine or fluorine atoms; and $R^2$ is a hydrogen atom or a chlorine, bromine or fluorine atom.

3. A compound according to claim 2 wherein $R^1$ is a chlorine, bromine or fluorine atom and $R^2$ is a hydrogen atom or a chlorine, bromine or fluorine atom.

4. A compound according to claim 3 wherein $R^1$ is a chlorine atom and $R^2$ is a hydrogen atom or a chlorine atom.

5. A compound according to claim 2 wherein Q is O and $R^4$ is a group of formula II in which Z is a bond or an oxygen atom.

6. A compound according to claim 5 wherein $R^4$ is 3-phenoxybenzyl group.

7. A compound according to claim 6 wherein $R^4$ is 4-fluoro-3-phenoxybenzyl group.

8. A compound according to claim 4 wherein $R^4$ is 6-phenoxypyridin-2-ylmethyl group.

9. An insecticidal or miticidal composition comprising an insecticidally or miticidally effective amount of a compound according to claim 1 and at least one inert carrier or surface-active agent.

10. A method of combatting insects or mites at a locus which comprises applying to the insects or mites or to the locus, an insecticidally or miticidally effective amount of a compound according to claim 1.

* * * * *

UNITED STATES PATENT AND TRADEMARK OFFICE
CERTIFICATE OF CORRECTION

PATENT NO. : 4,666,925
DATED : May 19, 1987
INVENTOR(S) : King Mo Sun

It is certified that error appears in the above—identified patent and that said Letters Patent is hereby corrected as shown below:

In Claim 1, Column 10, lines 45 and 46, delete: ", or $R^1$ and $R^2$ when taken together form a methylenedioxy group".

In Claim 9, Column 12, line 7, delete: "and at least one" and replace with -- in combination with an --.

Signed and Sealed this

First Day of March, 1988

Attest:

DONALD J. QUIGG

Attesting Officer     Commissioner of Patents and Trademarks